United States Patent [19]

Harbeke et al.

[11] Patent Number: 4,805,187
[45] Date of Patent: Feb. 14, 1989

[54] DETERMINATION OF SUBSTRATE TEMPERATURE USED DURING OXYGEN IMPLANTATION OF SIMOX WAFER

[75] Inventors: Guenther Harbeke, Affoltern am Alhis, Switzerland; Lubomir L. Jastrzebski, Plainsboro, N.J.

[73] Assignee: General Electric Company, Schenectady, N.Y.

[21] Appl. No.: 108,656

[22] Filed: Oct. 15, 1987

[51] Int. Cl.$^4$ ............................................... G01J 5/00
[52] U.S. Cl. .................................................... 374/123
[58] Field of Search ................. 374/123, 110, 121, 45, 374/129, 134; 283/1 A

[56] References Cited

U.S. PATENT DOCUMENTS 4,708,677 11/1987 Blank et al. .................... 374/123

OTHER PUBLICATIONS

M. J. Kim et al., "Surface Restoration of Oxygen-Implanted Silicon," *Journal of Applied Physics*, 54(4), Apr. 1983, pp. 1991-1999.

*Primary Examiner*—Roy N. Envall, Jr.
*Attorney, Agent, or Firm*—William Squire; James C. Davis, Jr.; Paul R. Webb, II

[57] ABSTRACT

The present invention provides graphs and a method of using the graphs to determine the substrate temperature used during oxygen implantation of SIMOX wafers. The method establishes a relationship between the wavelength of minimum transmittance for infrared energy and the implantation temperature. Such relationships are then expressed, in the form of graphs, for various selected oxygen dose and energy levels.

6 Claims, 3 Drawing Sheets

DETERMINATION OF SUBSTRATE TEMPERATURE USED DURING OXYGEN IMPLANTATION OF SIMOX WAFER

This invention was made with Government support under contract number F19628-86-C-0086, awarded by the Department of the Air Force. The Government has certain rights in this invention.

The present invention relates to an article and method for determining the substrate temperature that was used during the oxygen implantation phase in the manufacture of SIMOX wafers.

BACKGROUND OF THE INVENTION

Among various Silicon on Insulation (SOI) approaches SIMOX (separation by oxygen implantation) seems to be the most promising as a replacement for use of silicon on sapphire (SOS) in CMOS processing. During the SIMOX process oxygen at the dose of about $1.0$–$2.0 \times 10^{18}$ oxygen atoms $cm^{-2}$ is implanted into a silicon wafer with energy of about 150–200 Kev, within the ideal temperature range of from about 450° C. to about 650° C. To remove the implantation damage and to form a buried oxide, the SIMOX wafers are subsequently annealed at a temperature in the range from 1150° C. to 1400° C. A typical SIMOX structure is shown in FIG. 1 wherein a wafer 10 includes an oxygen implanted layer 12 and a regrown SIMOX film 14. A thin surface layer ($\simeq$10–20 nm) of the SIMOX wafers serves as a seed during the solid state regrowth process. The degree of crystalline perfection of this layer will influence the crystallographic perfection of the regrown SIMOX film 14.

While the implantation dose and voltage, which determine the thickness of both the buried oxide layer and the top silicon layer are important, they are somewhat easily monitored and controlled. The implantation temperature, on the other hand, is of crucial importance and is difficult to monitor and, therefore, difficult to control. It is well known that the crystallographic structure of the SIMOX films is determined by the implantation temperature, especially in the formation of a polysilicon electric field shielding layer, after post-implantation annealing. Also, the formation of thermal donors is related to this temperature. Adverse effects which occur when the implantation temperature substantially deviates from the ideal range of temperatures will remain in the film even after subsequent processing. For example, where the substrate temperature falls below about 440° C., amorphism will occur in SIMOX film. On the other hand, when the temperature exceeds about 670° C., the SIMOX film will become polycrystalline.

The determination of the substrate temperature used during implantation, at a time subsequent to actual implantation is difficult. However, there is a need for such a determination which will enable the selection of only high quality SIMOX wafers for further processing. This will greatly increase yield and reliability of completed devices and substantially reduce costs.

SUMMARY OF THE INVENTION

The present invention includes a plurality of graphs and a method for utilizing the graphs for examining a SIMOX wafer to determine the substrate temperature used during oxygen implantation. Each of the graphs represent a relationship between a wavelength of minimum transmittance of infrared radiation through a SIMOX wafer and the substrate temperature used during oxygen implantation of the wafer. The graphs may take the form of plots on a chart or a representation of the information in the graph retrievably stored in a computer accessible memory. Further, each graph is related to a particular dose of oxygen and energy level. Infrared energy having a spectrum of wavelengths spanning the range of from about 1000 $cm^{-1}$ to about 1100 $cm^{-1}$ is transmitted through a portion of the SIMOX wafer and the wavelength of minimum transmittance is determined. The dose of oxygen and energy used during oxygen implantation of the SIMOX wafer is determined and a graph corresponding to these two parameters is selected. The substrate temperature corresponding to the wavelength of minimum transmittance is determined as indicated by the graph.

DESCRIPTION OF THE PREFERRED EMBODIMENT

Figure 1:
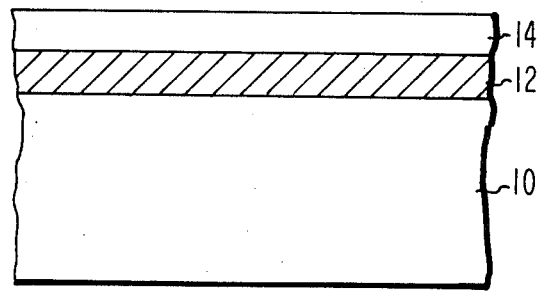
FIG. 1 is a partial cross-sectional view of a prior art SIMOX wafer.
Figure 2:
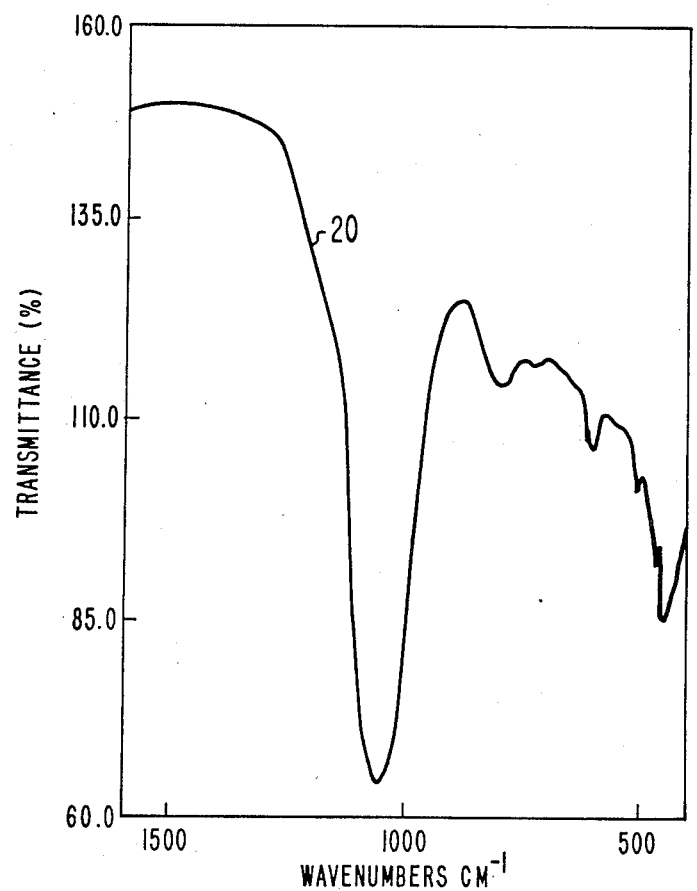
FIG. 2 is a plot showing percent transmittance within a selected range of infrared energy in SIMOX.
Figure 3:
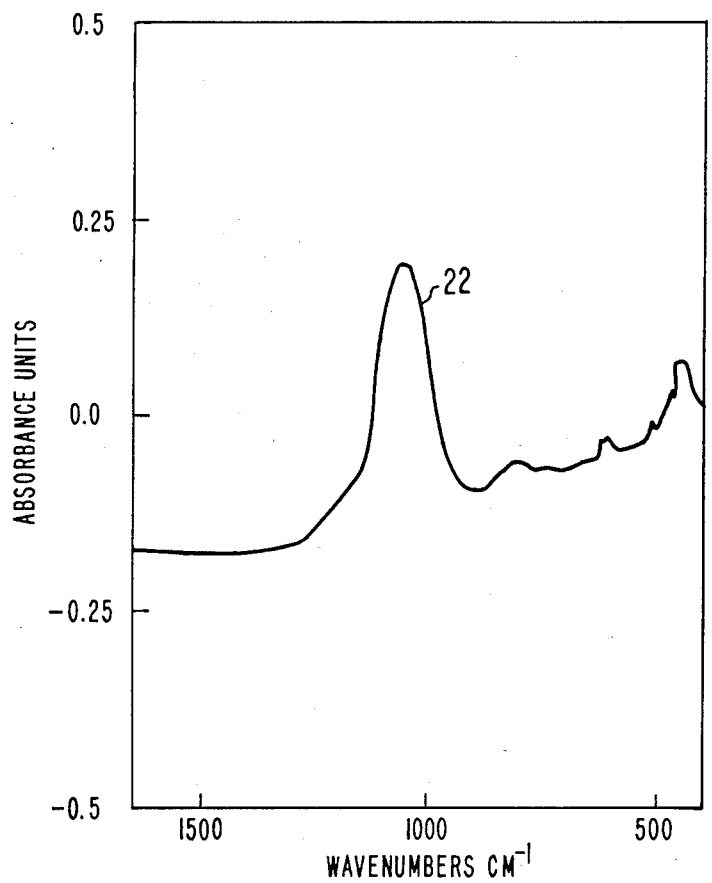
FIG. 3 is similar to the plot of FIG. 2 but showing absorbance.
Figure 4:
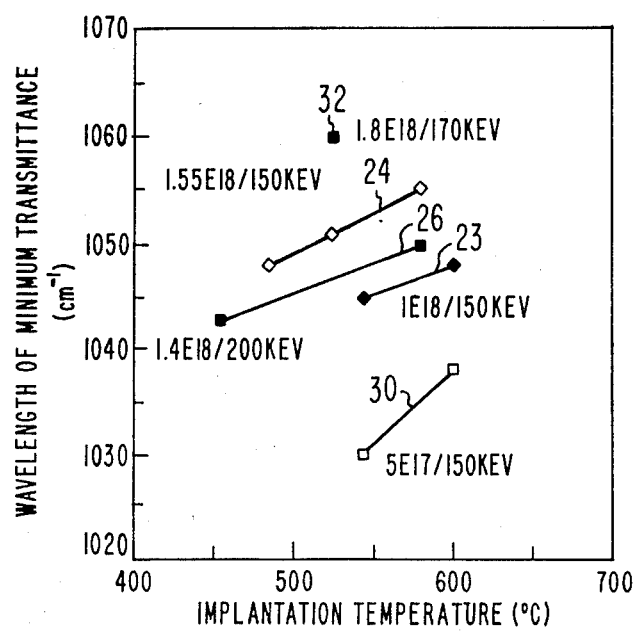
FIG. 4 is a chart showing several plots relating wavelength of minimum transmittance with implantation temperature for several sample wafers.

The optical transmission of a SIMOX wafer may be measured in the range from 4000 $cm^{-1}$ to 400 $cm^{-1}$ with reference to an oxygen-free silicon wafer using a Fourier Transform Infrared Spectrometer 113 V, manufactured by Bruker Analyticche Messiechnik, Karlsruhe, FRG. FIG. 2 includes a graph 20 which shows transmittance in the range from 1600 $cm^{-1}$ to 400 $cm^{-1}$ with absorption bands due to the vibration modes of silicon-oxygen bonding. Apparent transmittance values above 100% are due to differences in the scattering loss at the unpolished back side of sample and reference wafers. FIG. 3 includes a graph 22 which shows the corresponding absorbance $A = \log (I/T)$. With reference to FIG. 4, the peak positions of the main absorbance peak, or, position of minimum transmittance, in the range of 1020 $cm^{-1}$ to 1070 $cm^{-1}$ for several samples have been plotted as a function of implant temperature and are indicated as graphs 24, 26, 28 and 30. As is well known, this absorbtion band is due to the antisymmetric stretching vibration of the Si—O—Si local bonding unit of $SiO_2$. Its eigenfrequency is stochiometric $SiO_2$ has been quoted in the literature to be 1075 $cm^{-1}$, however, from our own measurements on thermally grown $SiO_2$ we found a frequency of 1089 $cm^{-1}$. In suboxides, i.e., $SiO_x$ with $x < 2$, there is a shift of the vibrational frequency to smaller wavenumbers with decreasing x. As the oxide moves off stochiometry, the silicon atoms have a higher probability of having one or more silicon atom neighbors and this change in the chemical environment shifts the Si—O—Si stretching frequency. On as-implanted SIMOX wafers there is a vibration frequency decrease that occurs as a function of implant temperature. Therefore, the lower the implant temperature, the more sub-oxide material is formed. We use these efforts for a post-implant determination of the implant temperature. Note, that the temperatures given in FIG. 4 have been measured by thermocouples attached to the wafer.

In order to achieve a post-implant determination of the implantation temperature, a series of sample wafers must be oxygen implanted under controlled conditions and the implantation temperatures, energy levels, and dose levels monitored. The series of sample wafers should be implanted at various energy and dose levels corresponding to those levels which are expected to be encountered in the post-implant testing. Each sample wafer is then exposed to infrared energy having a spectrum of wavelengths spanning the range of about 1000 $cm^{-1}$ to about 1100 $cm^{-1}$. Using the 113 V spectrometer, the wavelength of minimum transmittance of the infrared energy having transmitted through the sample wafer is determined. This can easily be determined within about $\pm 1$ wavenumber. The data from these sample wafers are then arranged to represent a relationship for each particular dose and energy level, between a wavelength of minimum transmittance and the actual temperature used during oxygen implantation of the sample wafers. The arrangement which represents, or defines, this relationship may take the form of a chart containing a plot or graph, or it may be a mathematical expression or logical expression that would be suitable for storing in a computer accessible memory. Such computer accessible memory includes, for example, magnetic and optical storage medium as well as ROM and RAM memory and other suitable memory devices. Since these relationships can be arranged in the form of a graph or mathematical or logical expression, all such arrangements will be referred to herein as graphs. It will be understood that the word graph will not be limited in any way to mean a particular arrangement or form of the so defined relationship.

Figure 5:
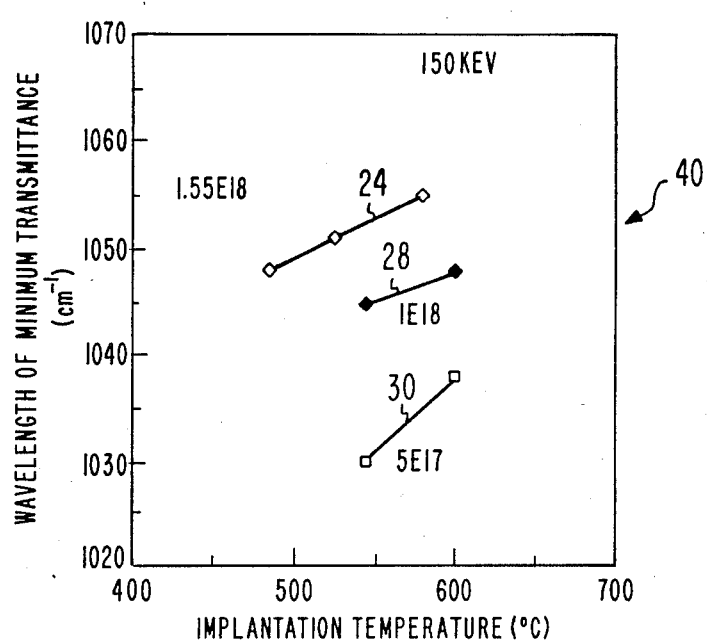
FIGS. 5, 6 and 7 are charts showing various groupings of the plots of FIG. 4.
Figure 6:
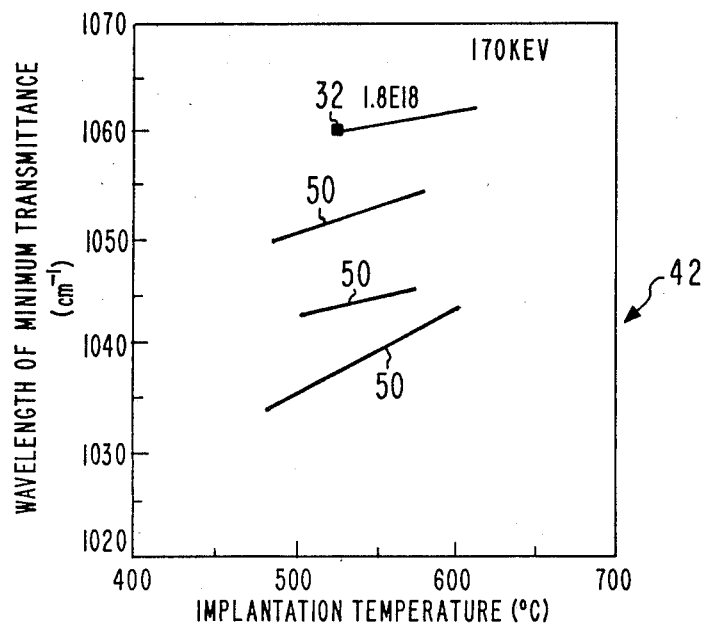
Figure 7:
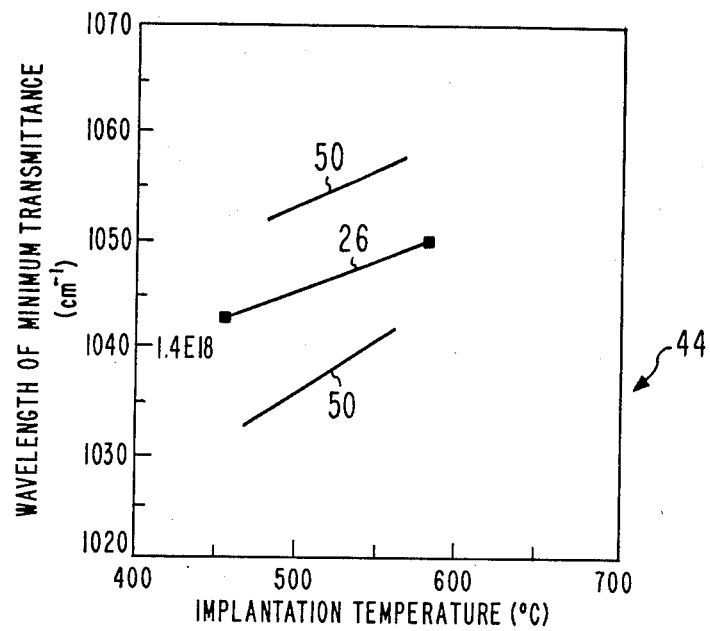

When relatively small quantities of SIMOX wafers are to be tested using the teachings of the present invention, it may be convenient to utilize charts which show the graphs in plot form. By way of example, FIGS. 5, 6 and 7 depict charts 40, 42, and 44, respectively, which show convenient groupings of the graphs 24 through 32 of FIG. 4. Such convenient groupings may include those graphs having a common implantation energy level, as in the present example, a common implantation dose of oxygen atoms, or some other desirable grouping. FIG. 5 includes the three graphs 24, 28 and 30 which represent the relationship between the peak wavelengths of minimum transmittance and the substrate temperature during oxygen implantation of three sample SIMOX wafers. All three of the wafers were implanted at an energy level of 150,000 electron volts at doses of $1.55 \times 10^{18}$, $1 \times 10^{18}$, and $5 \times 10^{17}$ oxygen atoms per square centimeter as indicated by the graphs 24, 28 and 30, respectively. The chart 40 includes a Y axis of ordinates depicting wavelengths spanning the range of from 1000 $cm^{-1}$ to 1100 $cm^{-1}$ and an X axis or abscissas depicting temperature spanning the range of from 400° C. to 700° C. The charts 42 and 44 show groups of graphs of wafers which were implanted at energy levels of 170,000 and 200,000 electron volts, respectively. While graphs 32 and 26 of the charts 42 and 44, respectively, represent actual test data taken from FIG. 4, additional similar graphs 50 representing different implantation doses of oxygen may be desirable. In all other respects, the charts 42 and 44 are similar to the chart 40. The selection of particular graphs for particular groups is done on the basis of convenience of use of the chart.

In certain cases it may be desirable to include particular graphs on a given chart irrespective of implantation energy or dose.

In utilizing charts to determine the implantation temperature that was used during oxygen implantation of a SIMOX wafer, the following simple steps would be performed. Using any suitable energy source, infrared energy having a spectrum of wavelengths spanning the range of from about 1000 $cm^{-1}$ to the 1100 $cm^{-1}$ is passed through a portion of the SIMOX wafer under test. By means of the 113 V spectrometer, the wavelength of minimum transmittance of the infrared energy being transmitted through the wafer is determined. The dose and energy level used during the oxygen implantation of the wafer is determined by using well known techniques. For example, both dose (concentration) and depth of the implant may be monitored by means of a Rutherford Backscattering Spectrometer (RBS) or by optical methods based on infrared and visible light reflections and infrared absorbtion. A chart is then selected having a graph which indicates a dose and energy level similar to that of the wafer under test. For example, assume that the dose and energy level of the test wafer is determined to be $5 \times 10^{17} Cm^{-2}$ and 150 Kev, respectively. Chart 40 of FIG. 5 would then be selected and graph 30 utilized. The wavelength of minimum transmittance, which was previously determined, is then located on the Y axis of the chart 40. Assume, for example, a wavelength of 1035 $cm^{-1}$. The temperature 575° C. on the X axis corresponding to the wavelength 1035 $cm^{-1}$ is determined in the usual manner. Therefore, in the present example, a temperature of approximately 575° C. was used during oxygen implantation of the SIMOX wafer under test. It is pointed out that since the wavelength of 1035 $cm^{-1}$ is accurate to within about one wavenumber, the determined implantation temperature of 575° C. will be accurate to within about $\pm 10°$ C.

It will be appreciated by those skilled in the art that post-implant determination of the implantation temperature may be accomplished by a computer or other suitable apparatus having access to the correct graph contained in storage. In such case, similar steps to those described above for the use of charts would be performed. That is, the dose and energy level is determined and a specific graph selected based thereon, the wavelength of minimum transmittance is measured, and based on the graph, a temperature corresponding to the wavelength is determined. These steps may be partially or completely automated for high speed testing of SIMOX wafers in a production environment.

An important advantage of the present invention is that a relatively simple but accurate method is provided for the post-implant determination of the implantation temperature of a SIMOX wafer. Such a determination is crucial in the selection of high quality SIMOX wafers prior to committing substantial time and expense to fabricating semiconductor devices. Additionally, utilization of the graphs and method of the present invention is non-destructive to the wafer and, therefore, permits 100% inspection where such is desirable.

What is claimed is:

1. In a method for examining a SIMOX wafer to determine the substrate temperature used during oxygen implantation, the steps comprising:
   (1) creating a plurality of graphs, each of which represents a relationship between a wavelength of minimum transmittance through a SIMOX wafer and the substrate temperature used during oxygen implantation of said wafer, each of said plurality of graphs, representing said relationship for a different particular dose of oxygen within the range of about $10^{17}$ oxygen atoms $cm^{-2}$ to about $2 \times 10^{18}$ oxygen atoms $cm^{-2}$ and a different particular energy level within the range of about 130 Kev to about 220 Kev, wherein, said wavelength of minimum transmittance covers a continuous spectrum of wavelengths spanning the range of from about 1000 $cm^{-1}$ to about 1100 $cm^{-1}$ and the substrate temperature spans a continuous range of temperatures from about 400° C. to about 700° C.; then (a) transmitting through a portion of said SIMOX wafer, infrared energy having a spectrum of wavelengths spanning the range of from about 1000 $cm^{-1}$ to about 1100 $cm^{-1}$;

(b) determining the wavelength of minimum transmittance of said infrared energy;

(c) determining the dose of oxygen and energy level used during said oxygen implantation of said SIMOX wafer; and (d) selecting one of said plurality of graphs corresponding to said dose and energy level of step (c) and determining said substrate temperature corresponding to said wavelength of minimum transmittance of step (b) as indicated by said one graph.

2. The method of claim 1 including a computer accessible memory having a representation of said plurality of graphs retrievably stored therein.

3. In a method for examining a SIMOX wafer to determine the substrate temperature used during oxygen implantation, the steps comprising:

(1) creating a plurality of graphs, each of which represents a relationship between a wavelength of minimum transmittance through a SIMOX wafer and the substrate temperature used during oxygen implantation of said wafer, each of said plurality of graphs, representing said relationship for a different particular dose of oxygen within the range of about $10^{17}$ oxygen atoms $cm^{-2}$ to about $2 \times 10^{18}$ oxygen atoms $cm^{-2}$ and a different particular energy level within the range of about 130 Kev to about 220 Kev, wherein, said wavelength of minimum transmittance covers a continuous spectrum of wavelengths spanning the range of from about 1000 $cm^{-1}$ to about 1110 $cm^{-1}$ and the substrate temperature spans a continuous range of temperatures from about 400° C. to about 700° C.;

(2) creating a chart having a group of said plurality of graphs depicted thereon, said chart including a Y axis of ordinates depicting wavelengths spanning the range of from about 1000 $cm^{-1}$ to about 1100 $cm^{-1}$ and an X axis of abscissas depicting temperature spanning the range of from about 400° C. to about 700° C.; then (a) transmitting through a portion of said SIMOX wafer, infrared energy having a spectrum of wavelengths spanning the range of from about 1000 $cm^{-1}$ to about 1100 $cm^{-1}$;

(b) determining the wavelength of minimum transmittance of said infrared energy;

(c) determining the dose of oxygen and energy level used during said oxygen implantation of said SIMOX wafer; and (d) selecting said chart having one of said plurality of graphs corresponding to said dose and energy level of step (c), locating said wavelength of minimum transmittance of step (b) on said chart, and determining the indicated substrate temperature on said chart corresponding to said located wavelength as indicated by said one graph.

4. The method of claim 3 wherein said group of graphs comprises those graphs related to a particular implantation energy level.

5. The method of claim 3 wherein said group of graphs comprises those graphs related to a particular dose of oxygen.

6. In a method for examining a SIMOX wafer to determine the substrate temperature used during oxygen implantation, the steps comprising:

(1) retrievably storing in computer memory a representation of a plurality of graphs, each graph representing a relationship between a wavelength of minimum transmittance through a SIMOX wafer and the substrate temperature used during oxygen implantation of said wafer, each of said plurality of graphs, representing said relationship for a different particular dose of oxygen within the range of about $10^{17}$ oxygen atoms $cm^{-2}$ to about $2 \times 10^{18}$ oxygen atoms $cm^{-2}$ and a different particular energy level within the range of about 130 Kev to about 220 Kev, wherein, said wavelength of minimum transmittance covers a continuous spectrum of wavelengths spanning the range of from about 1000 $cm^{-1}$ to about 1100 $cm^{-1}$ and the substrate temperature spans a continuous range of temperatures from about 400° C. to about 700° C.; then (a) transmitting through a portion of said SIMOX wafer, infrared energy having a spectrum of wavelengths spanning the range of from about 1000 $cm^{-1}$ to about 1100 $cm^{-1}$;

(b) determining the wavelength of minimum transmittance of said infrared energy;

(c) determining the dose of oxygen and energy level used during said oxygen implantation of said SIMOX wafer; and (d) selecting one of said plurality of graphs corresponding to said dose and energy level of step (c) and determining said substrate temperature corresponding to said wavelengths of minimum transmittance of step (b) as indicated by said retrieved representation.

* * * * *